United States Patent
Kim et al.

(10) Patent No.: US 12,102,985 B2
(45) Date of Patent: Oct. 1, 2024

(54) METAL PARTICLE-LOADED HOLLOW MESOPOROUS ORGANOSILICA NANO/MICROPARTICLES AND METHOD FOR MANUFACTURING SAME

(71) Applicant: PUSAN NATIONAL UNIVERSITY INDUSTRY UNIVERSITY COOPERATION FOUNDATION, Busan (KR)

(72) Inventors: Jae Hyuk Kim, Busan (KR); Hak Lae Lee, Busan (KR)

(73) Assignee: PUSAN NATIONAL UNIVERSITY INDUSTRY UNIVERSITY COOPERATION FOUNDATION, Busan (KR)

( * ) Notice: Subject to any disclaimer, the term of this patent is extended or adjusted under 35 U.S.C. 154(b) by 452 days.

(21) Appl. No.: 17/312,246

(22) PCT Filed: Feb. 21, 2020

(86) PCT No.: PCT/KR2020/002546
§ 371 (c)(1),
(2) Date: Jun. 9, 2021

(87) PCT Pub. No.: WO2020/180029
PCT Pub. Date: Sep. 10, 2020

(65) Prior Publication Data
US 2022/0023841 A1 Jan. 27, 2022

(30) Foreign Application Priority Data
Mar. 6, 2019 (KR) .................. 10-2019-0025726

(51) Int. Cl.
*B01J 23/52* (2006.01)
*A61K 9/51* (2006.01)
(Continued)

(52) U.S. Cl.
CPC ............ *B01J 23/52* (2013.01); *A61K 9/5115* (2013.01); *B01J 21/08* (2013.01); *B01J 23/44* (2013.01);
(Continued)

(58) Field of Classification Search
CPC .................. B01J 21/08; B01J 23/52
See application file for complete search history.

(56) References Cited

PUBLICATIONS

Wei et al, A Versatile In-Situ Etching-Growth Strategy for Synthesis of Yolk-Shell Structured Periodic Mesoporous Organosilica Nanocomposites, RSC Advances, vol. 6, pp. 51470-51479. (Year: 2016).*

(Continued)

*Primary Examiner* — Carlos A Azpuru
(74) *Attorney, Agent, or Firm* — NORTON ROSE FULBRIGHT US LLP

(57) ABSTRACT

A hollow mesoporous organic silica nano/microparticle having metal particles deposited thereon, and a method for preparing the same. The method may prepare a spherical nanoparticle by coating a porous organic silica layer on an inorganic silica particle having the metal particles deposited thereon and via selective etching of the layer. In addition, two or more types of metals pre-synthesized together with a magnetic particle, or different shapes of metals may be deposited on the nanoparticle at a target concentration. Thus, the nano/microparticle may be used for a drug delivery matrix, a catalyst, and a photothermal effect.

20 Claims, 9 Drawing Sheets

(51) Int. Cl.
*B01J 21/08* (2006.01)
*B01J 23/44* (2006.01)
*B01J 23/745* (2006.01)
*B01J 31/02* (2006.01)
*B01J 35/00* (2006.01)
*B01J 35/33* (2024.01)
*B01J 35/60* (2024.01)
*B01J 37/02* (2006.01)
*B01J 37/04* (2006.01)
*B01J 37/06* (2006.01)

(52) U.S. Cl.
CPC ......... *B01J 23/745* (2013.01); *B01J 31/0237* (2013.01); *B01J 35/19* (2024.01); *B01J 35/33* (2024.01); *B01J 35/60* (2024.01); *B01J 37/0217* (2013.01); *B01J 37/04* (2013.01); *B01J 37/06* (2013.01)

(56) References Cited

PUBLICATIONS

Liberman et al, Synthesis and Surface Functionalization of Silica Nanoparticles for Nanomedia, Surf Sci Rep, 6992-3): 132-158 (Year: 2014).*
English translation of Written Opinion for International Application No. PCT/KR2020/002546 mailed on Jun. 9, 2020.
International Search Report and Written Opinion corresponding to International Application No. PCT/KR2020/002546 mailed on Jun. 9, 2020 with English translation of the International Search Report.
Wei, Y. et al. "A versatile in situ etching-growth strategy for synthesis of yolk-shell structured periodic mesoporous organosilica nanocomposites" RSC Advances, 2016, vol. 6, pp. 51470-051479.

* cited by examiner

[FIG. 1]
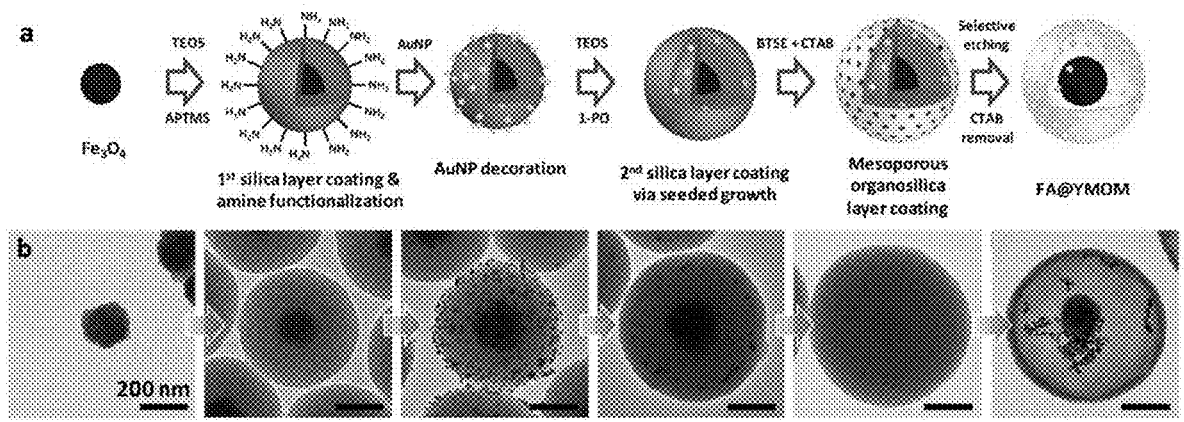
[FIG. 2]
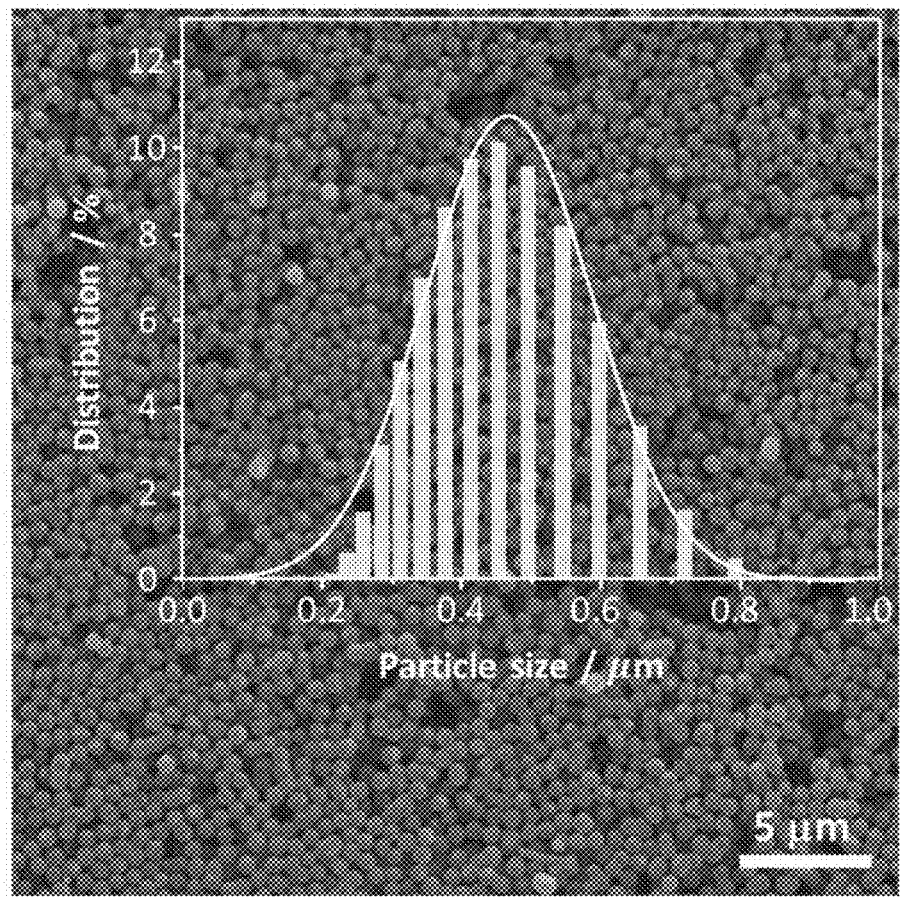

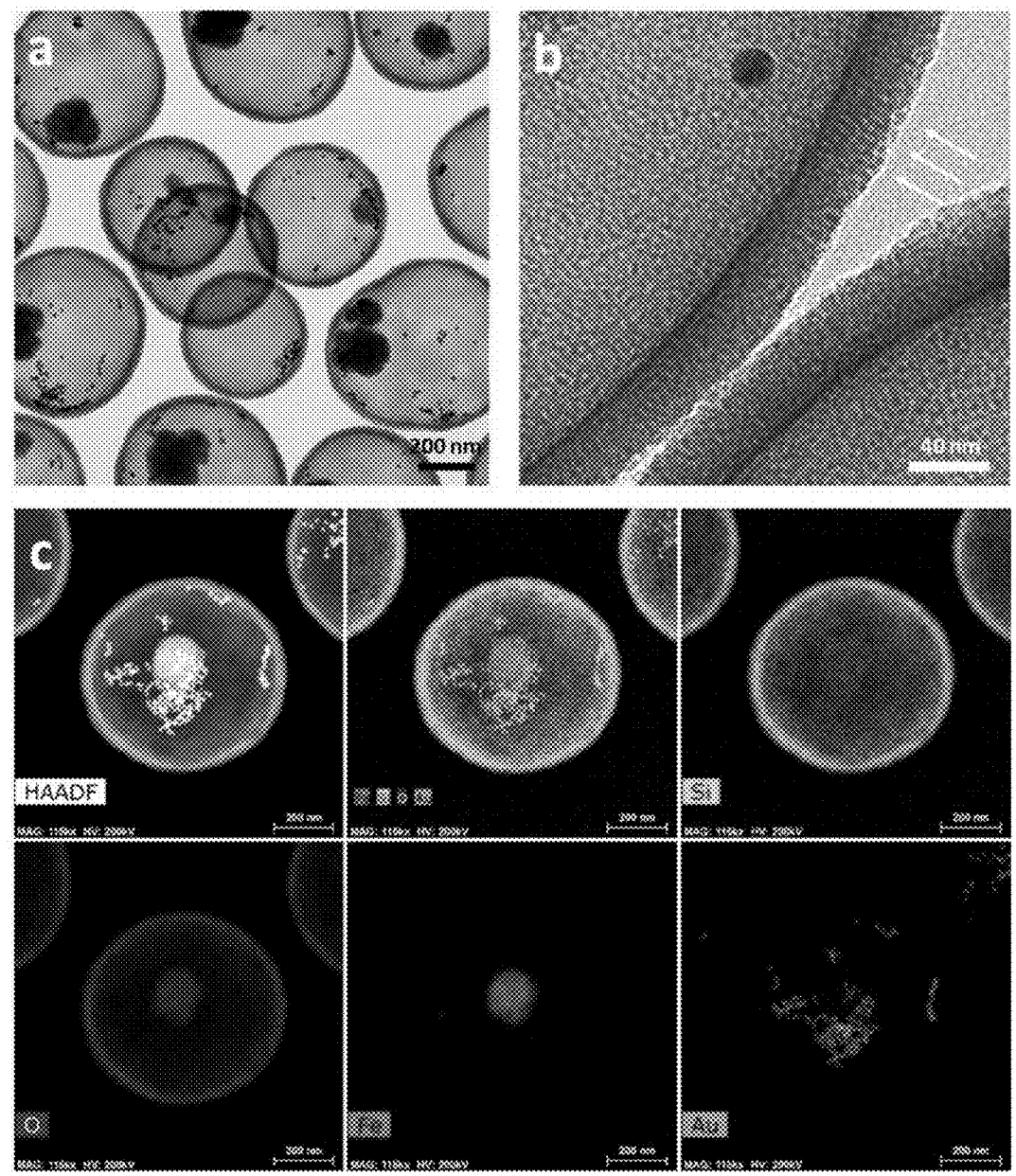
[FIG. 3]

[FIG. 4]
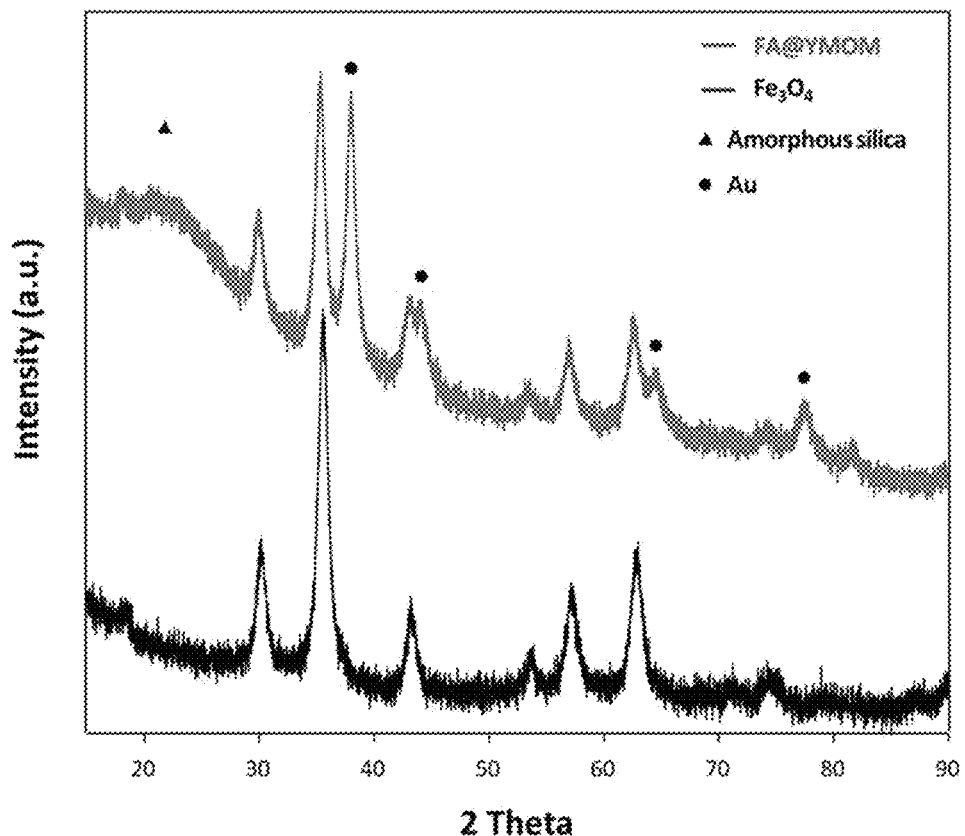
[FIG. 5]
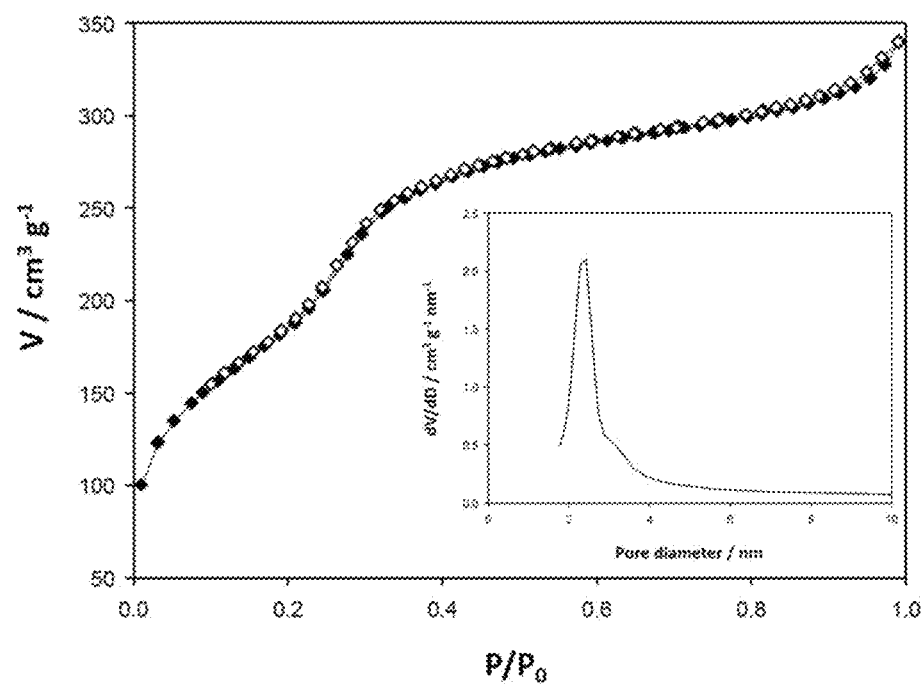

[FIG. 6]
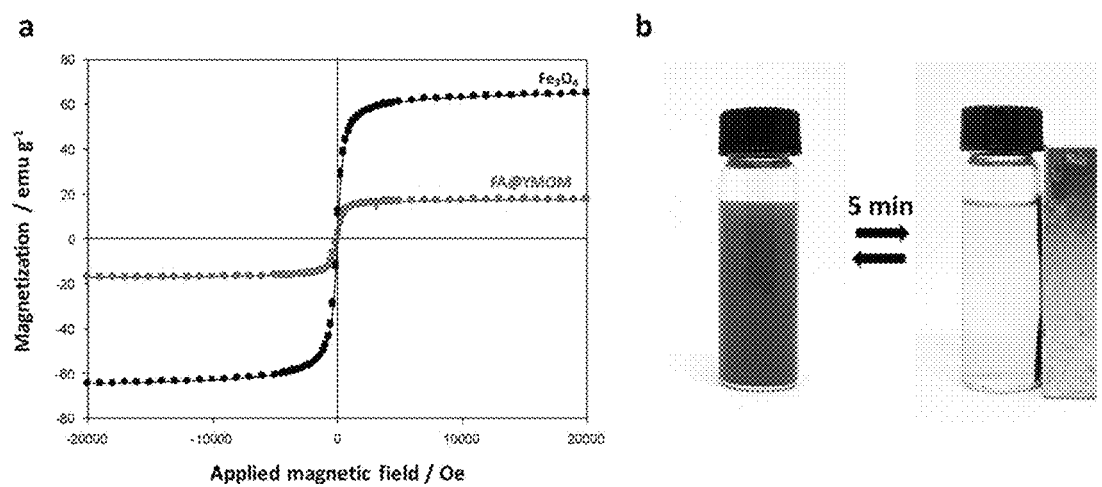
[FIG. 7]
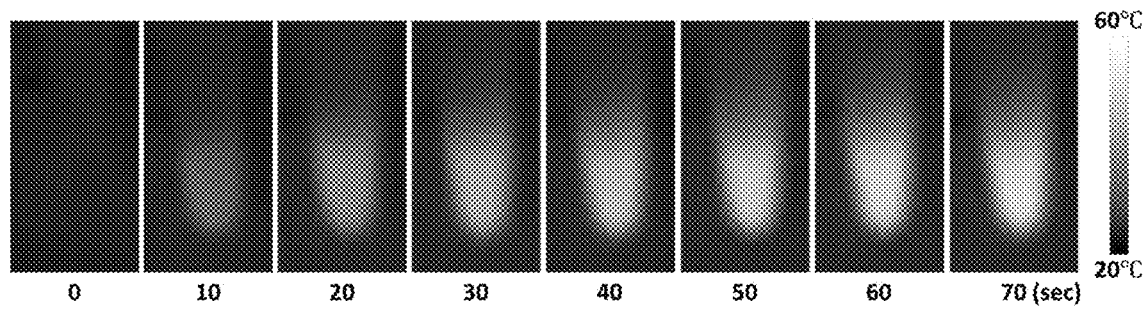

[FIG. 8]
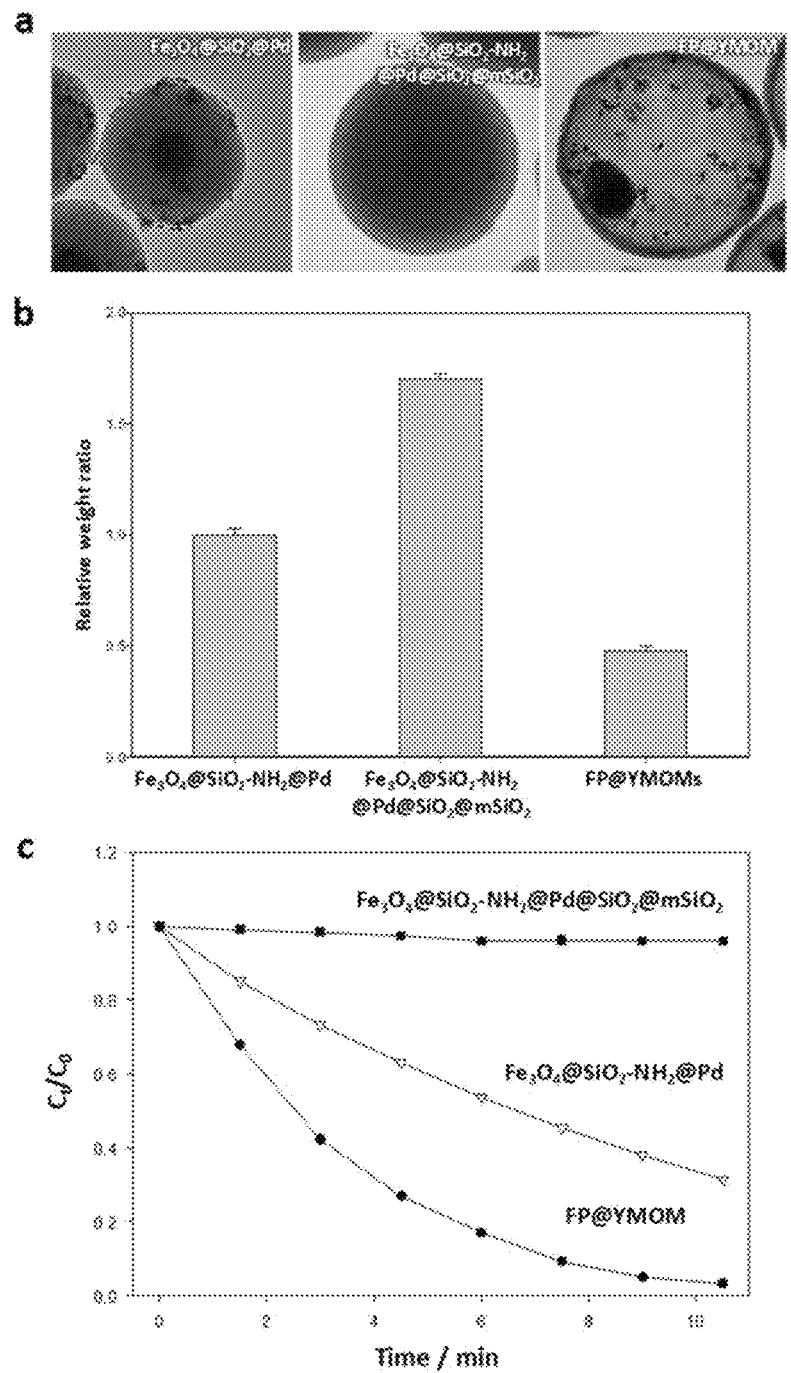

[FIG. 9]
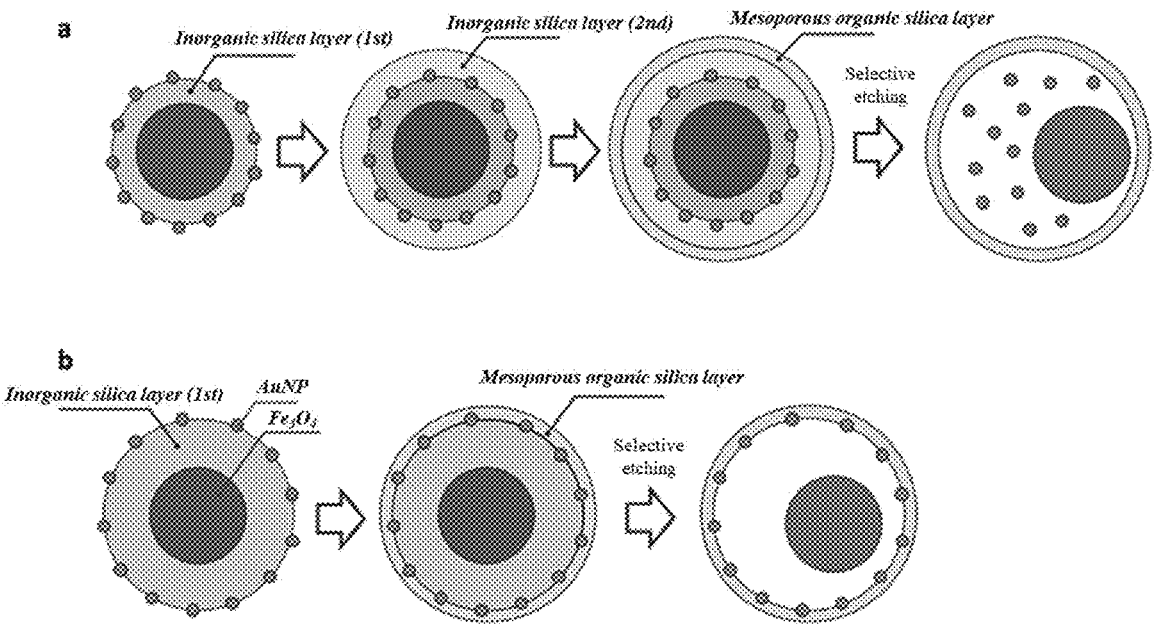
[FIG. 10]
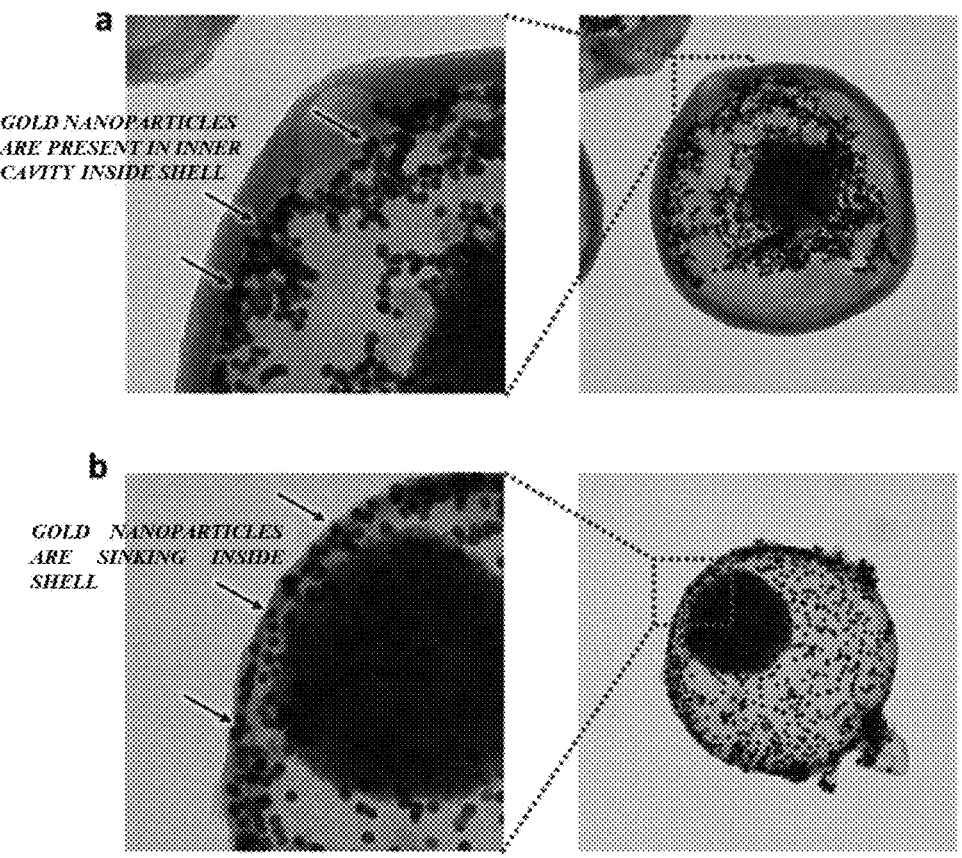

[FIG. 11]
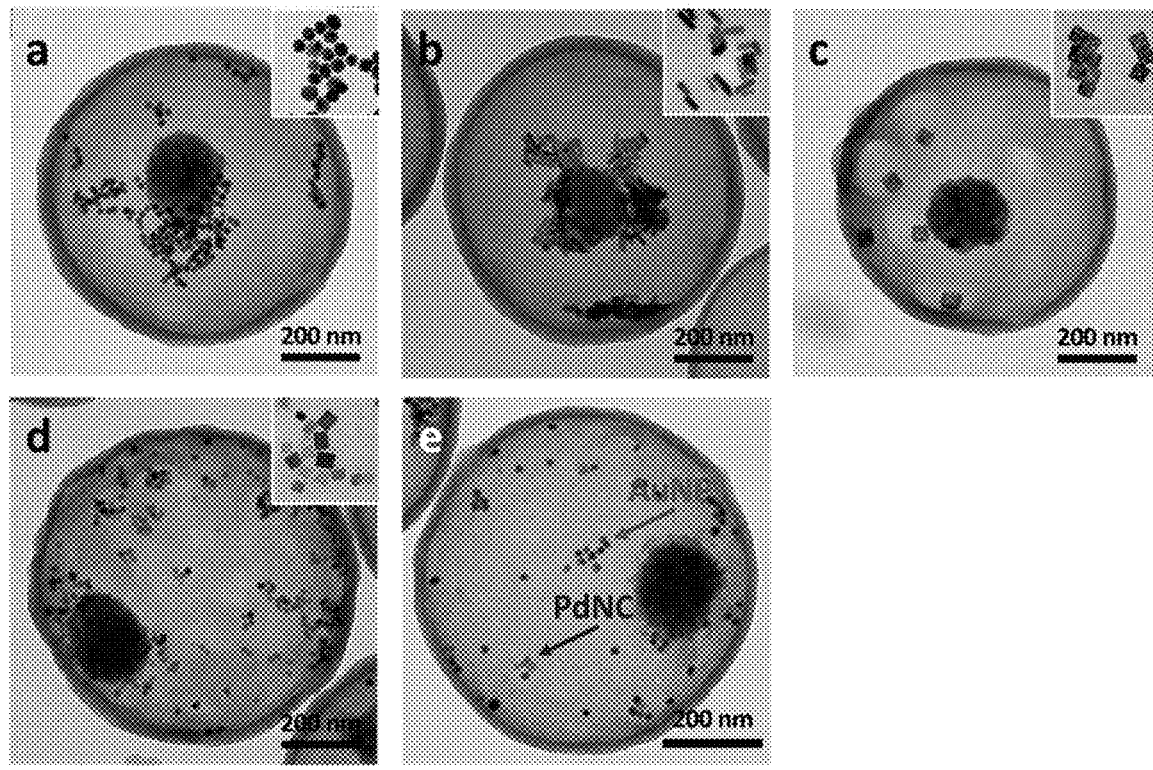
[FIG. 12]
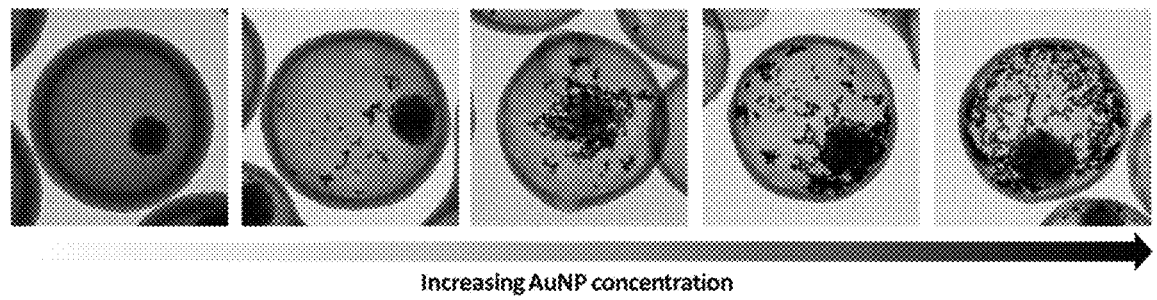

[FIG. 13]
A. SCHEMATIC DIAGRAM OF PREPARATION PROCESS OF PHOTO-STIMULATIVE DRUG RELEASING MATERIAL
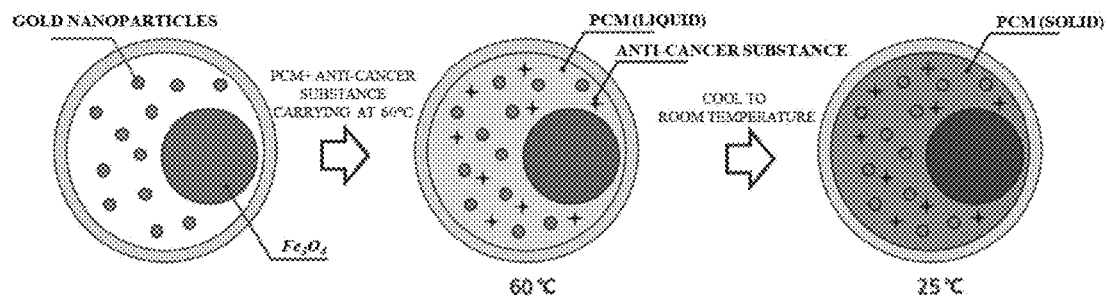
B. UTILIZATION OF PHOTO-STIMULATIVE DRUG RELEASING MATERIAL
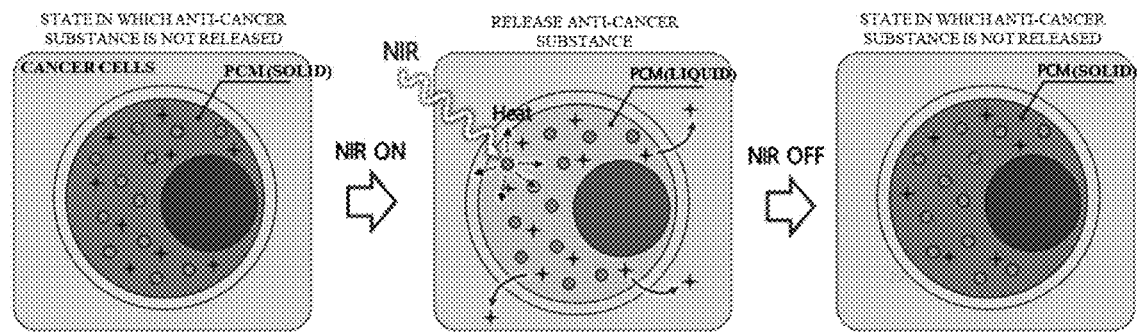

[FIG. 14]
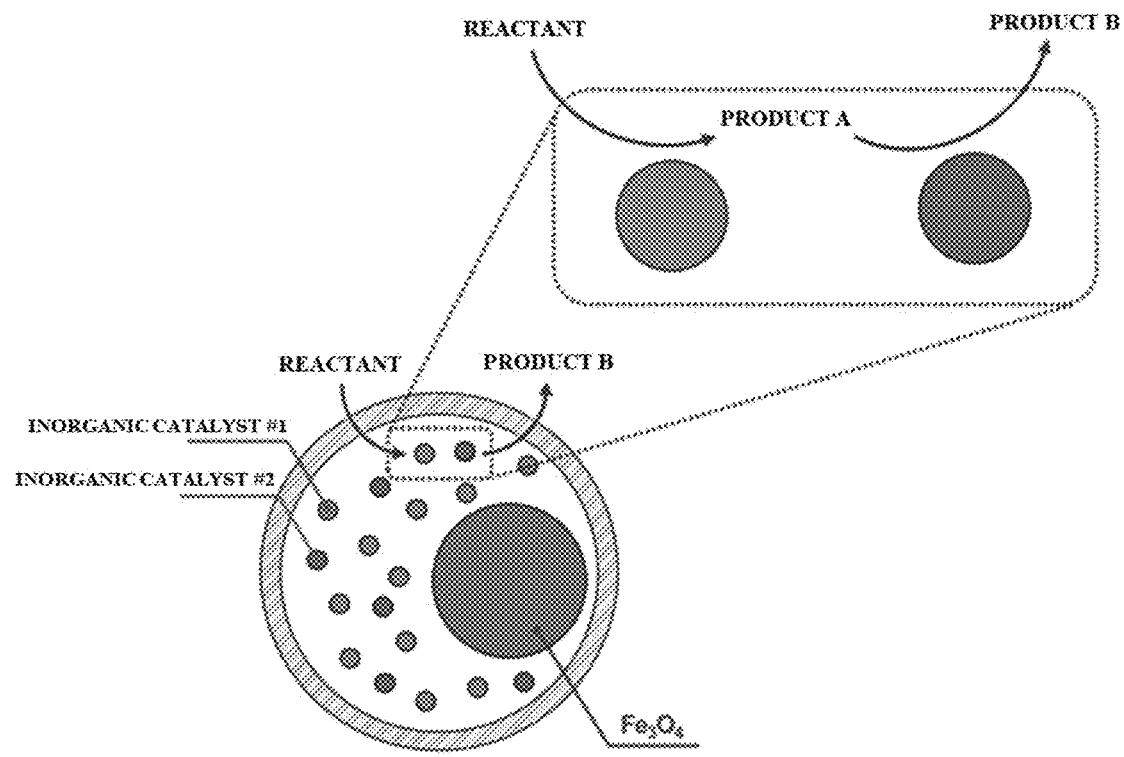

METAL PARTICLE-LOADED HOLLOW MESOPOROUS ORGANOSILICA NANO/MICROPARTICLES AND METHOD FOR MANUFACTURING SAME

CROSS REFERENCE TO RELATED APPLICATIONS

This application is a national phase under 35 U.S.C. § 371 of International Application No. PCT/KR2020/002546, filed Feb. 21, 2020, which claims the benefit of priority to Korean Patent Application Serial No. 10-2019-0025726, filed Mar. 6, 2019, the entire contents of each of which are hereby incorporated by reference in their entirety.

FIELD OF THE INVENTION

The present disclosure relates to a hollow mesoporous organic silica nanoparticle having metal particles deposited thereon, and a method for preparing the same, and more specifically, to a hollow mesoporous organic silica nanoparticle having metal particles deposited thereon, and a method for preparing the same that may prepare a spherical nanoparticle using inorganic silica and organic silica, and may have various shapes and various types of metal particles deposited thereon using metal particles that have been synthesized.

DESCRIPTION OF RELATED ART

A mesoporous material refers to a material having pores of 2 to 50 nm among materials having a porous structure based on an arrangement of fine pores. Among those, mesoporous silica nanoparticles (hereinafter, MSNs), which are mesoporous materials based on silica, are simple and economical in a synthesis method thereof, have flexibility and biocompatibility to be synthesized in various sizes depending on an application, and have a large specific surface area compared to a volume. Thus, the MSNs are being used in various fields as an adsorbent, a catalyst, a sensor, an optical device, a drug delivery medium, a bio-imaging instrument, and the like.

Among the mesoporous silica nanoparticles, a hollow mesoporous silica nanoparticle (hereinafter, referred to as a HMSN) having a composite hollow silica structure is attracting attention. In the HMSN, a meso porous silica frame forms a shell of the nanoparticle, and the shell has a hollow structure. With the structure as described above, not only various materials may be deposited on the hollow, but also an internally deposited material may be protected from an external environment by the shell, and at the same time, a loss of the internally deposited material to the outside may be prevented. Thus, the HMSN is a material that has attracted great attention in recent years for an application to drug delivery matrix, catalyst, and energy reservoir technologies.

In recent years, further from such HMSN shape, a yolk-shell structured mesoporous silica nanoparticle (hereinafter, referred to as a YMSN), a structure in which various metal nanoparticles with magnetic or catalytic performance may move freely inside a core of the HMSN, has become a key technology for engineering application research using mesoporous nanostructures. The YMSN is very important for the study of the nanostructures because the YMSN has customized properties such as an empty space of a core in which synthesis and tuning may be performed, a high surface area, an accessible pore channel that is beneficial for adsorption and diffusion of guest molecules, and the like.

However, methods for synthesizing the YMSN having the metal nanoparticles deposited thereon reported so far have limitations in that shapes of the nanoparticles that may be deposited are very limited, and different types of metal nanoparticles are not able to be deposited on one capsule simultaneously. For example, when using gold as the metal nanoparticle to be deposited, with existing preparing methods, it is impossible to deposit special shapes of metal nanoparticles synthesized under very demanding conditions such as gold nanorods (hereinafter, referred to as GNRs) and Au nanocages (hereinafter, referred to as AuNCs). In detail, in an existing method for preparing the YMSN in which the HMSN is first synthesized, and then a metal nanoparticle precursor is added in this state to grow the metal nanoparticle, there are fatal limitations in that uniformity of the metal nanoparticles is very poor because a presence of the shell greatly limits a synthesis process of the metal nanoparticles, it is impossible to prepare a metal nanoparticle of an unusual shape involving several washing and synthesis processes, and it is uneconomical and requires additional work to separate the metal nanoparticles because the metal nanoparticles are synthesized not only inside the shell, but also outside the shell.

SUMMARY OF THE INVENTION

One purpose of the present disclosure is to provide a method for preparing a hollow mesoporous organic silica nano/microparticle having metal particles deposited thereon.

Another purpose of the present disclosure is to provide a hollow mesoporous organic silica nano/microparticle having metal particles deposited thereon.

A method for preparing a hollow mesoporous organic silica nano/microparticle having metal particles deposited thereon for one purpose of the present disclosure includes coating a porous organic silica layer on a surface of an inorganic silica particle having the metal particles deposited thereon, and selectively etching the inorganic silica.

In one implementation, the inorganic silica particle having the metal particles deposited thereon may be prepared by a method including modifying the surface of the inorganic silica particle with a metal-affinity functional group to prepare an inorganic silica particle having the metal-affinity functional group introduced on the surface of the inorganic silica, attaching the metal particles to the metal affinity functional group to prepare an inorganic silica particle with the metal particles attached thereto, and coating an inorganic silica layer on the inorganic silica particle with the metal particles attached thereto.

In one implementation, a seed for first preparing the inorganic silica may be one selected from a group consisting of several tens of nano-sized inorganic silica, a magnetic nanoparticle, a metal oxide nanoparticle, and a metal nanoparticle.

In one implementation, the metal-affinity functional group may be one of an amine group and a thiol group.

In one implementation, the inorganic silica may be synthesized from tetraethyl orthosilicate (TEOS).

In one implementation, the metal-affinity functional group may be introduced from one selected from a group consisting of (3-aminopropyl)trimethoxysilane (APTMS), (3-aminopropyl)triethoxysilane (APTES), (3-mercaptopropyl)trimethoxysilane (MPTMS), and (3-mercaptopropyl)triethoxysilane (MPTES).

In one implementation, the coating of the inorganic silica layer on the inorganic silica particle with the metal particles attached thereto may include coating the inorganic silica layer to cover all of the metal particles.

In one implementation, the porous organic silica layer may have an open core.

In one implementation, the coating of the porous organic silica layer may be synthesized from solution of an organic silica precursor and a surfactant mixed with each other.

In one implementation, the organic silica precursor may be at least one or combinations of at least two selected from a group consisting of bis(triethoxysilyl)ethane (BTSE), bis(triethoxysilyl)ethylene (BTSEY), bis[3-(triethoxysilyl)tetrasulfide] (BTES), bis(triethoxysilyl)phenylene (BTEB), bis(triethoxysilyl)-biphenyl (BTEBP), 1,8-bis(triethoxysilyl) octane (BTEO), bis[3-(triethoxysilyl)propyl] tetrasulfide (BTEPT), and N,N-bis-[(3-triethoxysilylpropyl)aminocarbonylpolyethylene oxide] (BTEPEO).

In one implementation, the surfactant may be one selected from a group consisting of hexadecyltrimethylammonium bromide (CTAB), cetyltrimethylammonium chloride (CTAC), sodium dodecyl sulfate (SDS), polysorbates, and triton.

In one implementation, the selective etching may be performed by heating aqueous solution containing the dispersed inorganic silica particles.

In one implementation, the selective etching may be performed by heating basic aqueous solution containing the dispersed inorganic silica particles.

In one implementation, a basic component in the basic aqueous solution may be selected from a group consisting of sodium hydroxide, potassium hydroxide, tetramethylammonium hydroxide, ammonia, sodium carbonate, sodium hydrogen carbonate, potassium carbonate, and potassium hydrogen carbonate.

A hollow mesoporous organic silica nano/microparticle having metal particles deposited thereon for another purpose of the present disclosure is provided.

In one implementation, the metal particle may include at least two types of metal particles or different shapes of metal particles, wherein the at least two types of metal particles or the different shapes of metal particles may be deposited thereon the hollow mesoporous organic silica nano/microparticle.

In one implementation, the metal may be gold, and the nano/microparticle may be used for photothermal therapy.

In one implementation, the metal may be catalyst metal, and the nano/microparticle may be used as a catalyst.

In one implementation, the nano/microparticle may carry drug, and the nano/microparticle may be used as a drug carrier.

According to a hollow mesoporous organic silica nano/microparticle having metal particles deposited thereon, and a method for preparing the same of the present disclosure, the nano/microparticle may be prepared as a spherical nano/microparticle, and the deposited metal particles may be deposited at a desired concentration using various types of nano/microparticle nanorods, nano/micro cages, and the like, which have already been synthesized. Further, different shapes or different types of metal particles may be deposited on one hollow mesoporous organic silica nano/microparticle. Because the metal particles may independently exist in one hollow mesoporous organic silica nano/microparticle, the nano/microparticle may be used for a drug delivery matrix, a catalyst, and a photothermal therapy.

Further, in addition to the metal nanoparticles, magnetic particles with a magnetic property may be deposited together with the metal particles. Thus, in addition to a thromboplastin time (PTT), a biocatalytic reaction, magnetic resonance imaging (hereinafter, referred to as MRI), and particle recovery using the magnetic property are possible, so that various functions may be concentrated in one nano/micro structure.

BRIEF DESCRIPTION OF THE DRAWINGS

FIG. 1 is a view showing a method for preparing a hollow mesoporous organic silica nano/microparticle having metal particles and magnetic nanoparticles deposited thereon.

FIG. 2 is a scanning electron microscope image of $Fe_3O_4$/AuNP@YMOM prepared according to Example 1 of the present disclosure.

FIG. 3 is field-emission transmission electron microscopy images of $Fe_3O_4$/AuNP@YMOM prepared according to Example 1 of the present disclosure.

FIG. 4 is an image showing a XRD pattern of $Fe_3O_4$/AuNP@YMOM prepared according to Example 1 of the present disclosure.

FIG. 5 is a view showing a nitrogen sorption isotherm and a pore size distribution curve of $Fe_3O_4$/AuNP@YMOM prepared according to Example 1 of the present disclosure.

FIG. 6 is a view showing magnetic properties of $Fe_3O_4$/AuNP@YMOM prepared according to Example 1 of the present disclosure.

FIG. 7 shows thermal images of $Fe_3O_4$/AuNP@YMOM prepared according to Example 1 of the present disclosure.

FIG. 8 is a view showing catalytic reactions of $Fe_3O_4$/PdNP@YMOM and Comparative Samples prepared according to the present disclosure.

FIG. 9 is a view showing methods for preparing Sample-1 and Comparative Sample-1 prepared according to the present disclosure.

FIG. 10 shows TEM images of Sample-1 and Comparative Sample-1 prepared according to the present disclosure.

FIG. 11 shows TEM images of hollow mesoporous organic silica nano/microparticles having various types of metal particles deposited thereon prepared according to the present disclosure.

FIG. 12 shows TEM images of a hollow mesoporous organic silica nano/microparticle having metal particles with an increased content deposited thereon.

FIG. 13 is a view related to a photo-stimulative drug releasing material using a hollow mesoporous organic silica nano/microparticle prepared according to the present disclosure.

FIG. 14 is a view showing utilization as a tandem micro reactor of a hollow mesoporous organic silica nano/microparticle having metal particles deposited thereon according to the present disclosure.

DETAILED DESCRIPTIONS

Hereinafter, an embodiment of the present disclosure will be described in detail with reference to the accompanying drawings. The present disclosure may be variously modified and may take many forms. Thus, specific embodiments will be illustrated in the drawings and described in detail herein. However, the specific embodiments are not intended to limit the present disclosure thereto. It should be understood that all changes, equivalents thereto, or substitutes therewith are included in a scope and spirit of the present disclosure. In describing the drawing, similar reference numerals are used for similar components.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Method for Preparing a Hollow Mesoporous Organic Silica Nano/Microparticle Having Metal Particles Deposited Thereon The present disclosure provides a method for preparing a hollow mesoporous organic silica nano/microparticle having metal particles deposited thereon.

FIG. 1 is a view showing a method for preparing a hollow mesoporous organic silica nano/microparticle having metal particles and magnetic nanoparticles deposited thereon. a in FIG. 1 is a schematic diagram of step-by-step preparation of a method for preparing a hollow mesoporous organic silica nano/microparticle having metal particles and magnetic nanoparticles deposited thereon.

Referring to FIG. 1, the method of preparing the hollow mesoporous organic silica nano/microparticles having the metal particles deposited thereon of the present disclosure will be described in detail.

The method for preparing the hollow mesoporous organic silica nano/microparticles having the metal particles deposited thereon includes: coating a porous organic silica layer on a surface of an inorganic silica particle having the metal particles deposited thereon; and selectively etching the inorganic silica. The inorganic silica particle having the metal particles deposited thereon may be prepared by a method including: modifying the surface of the inorganic silica particle with a metal-affinity functional group to prepare an inorganic silica particle having the metal-affinity functional group introduced on the surface of the inorganic silica; attaching the metal particles to the metal affinity functional group to prepare an inorganic silica particle to which the metal particles are attached; and coating an inorganic silica layer on the inorganic silica particle to which the metal particles are attached.

Specifically, first, the prepared inorganic silica particle is prepared. The inorganic silica particle may be synthesized from tetraethyl ortho silicate (hereinafter, TEOS). In this connection, the inorganic silica particle may contain metal oxide therein. For example, the inorganic silica particle may contain magnetic nanoparticles, and preferably, the magnetic nanoparticles may be $Fe_3O_4$. The inorganic silica particle containing the metal oxide may be prepared by coating metal oxide nanoparticles with the inorganic silica using an inorganic silica precursor TEOS.

In order to attach the metal particles to the inorganic silica particle, the surface of the inorganic silica particle is modified with the metal-affinity functional group to prepare the inorganic silica particle onto which the metal-affinity functional group is introduced. The metal-affinity functional group may be one of an amine group and a thiol group, and the metal-affinity functional group may be introduced from one selected from a group consisting of (3-aminopropyl)trimethoxysilane (hereinafter, APTMS), (3-aminopropyl)triethoxysilane (hereinafter, APTES), (3-mercaptopropyl)trimethoxysilane (hereinafter, MPTMS), (3-mercaptopropyl)triethoxysilane (hereinafter, MPTES), and the like as precursors. Preferably, when the metal-affinity functional group is the amine group, the metal-affinity functional group may be introduced from one selected from a group consisting of the (3-aminopropyl)trimethoxysilane (hereinafter, the APTMS) and the (3-aminopropyl)triethoxysilane (hereinafter, the APTES). When the metal-affinity functional group is the thiol group, the metal-affinity functional group may be introduced from one selected from a group consisting of the (3-mercaptopropyl)trimethoxysilane (hereinafter, the MPTMS) and the (3-mercaptopropyl)triethoxysilane (hereinafter, the MPTES).

The inorganic silica particle to which the metal particles are attached is prepared by attaching the metal particles to the metal-affinity functional group of the inorganic silica onto which the metal-affinity functional group is introduced. The metal particles may be two or more types of metal, or metal particles of different shapes, and the metal particles may be in a form of a nanocube, a nanorod, a nanocage, and the like. As the metal, gold (Au), silver (Au), palladium (Pd), platinum (Pt), and the like may be used. The metal particles may be stirred in aqueous ethanol solution to be attached. For example, a palladium nanocube and a gold nanoparticle may be used as the metal particle.

The inorganic silica layer is additionally coated on the inorganic silica particle to which the metal particles are attached to prepare the inorganic silica particle having the metal particles deposited thereon. In this connection, the inorganic silica layer may be coated to cover all of the metal particles of the inorganic silica particle to which the metal particles are attached. When the inorganic silica layer is coated to only cover some of the metal particles, it is difficult to prepare a hollow mesoporous organic silica nano/microparticle having spherical metal particles deposited thereon because of exposed metal particles. In addition, the exposed metal particles sink into a mesoporous layer and the shell, which is an interface, in the process of the formation of the mesoporous shell, and are not able to be freely dispersed in an inner cavity of the hollow mesoporous organic silica nano/microparticle having the finally prepared metal particles deposited thereon, so that there is a problem that it is difficult to prepare a mesoporous shell having a high porosity.

The coating of the inorganic silica layer on the inorganic silica particle to which the metal particles are attached may be essential in preparing the hollow mesoporous organic silica nano/microparticles having the metal particles deposited thereon in an independently movable manner. In addition, the inorganic silica layer may be coated through seeded growth. Further, through the above step, the hollow mesoporous organic silica nano/microparticle capable of having various types of metal particles that have already been synthesized deposited thereon may be prepared.

In one implementation, the inorganic silica layer may be synthesized from the tetraethyl orthosilicate (hereinafter, the TEOS), in the same manner as the inorganic silica particle, and the silica layer may be coated with a seeded growth technique using the TEOS as the precursor.

A porous organic silica layer is coated on the inorganic silica layer present on the inorganic silica particle having the metal particles deposited thereon. The porous organic silica layer may be synthesized from solution in which an organic silica precursor and a surfactant are mixed with each other. The surfactant is used as a material that guides formation of a meso channel. In one implementation, hexadecyltrimethylammonium bromide (hereinafter, CTAB), cetyltrimethylammonium chloride (hereinafter, CTAC), sodium dodecyl sulfate (SDS), polysorbates, triton, and the like may be used as the surfactant. The organic silica precursor may one or combinations of at least two of bis(triethoxysilyl)ethane (hereinafter, BTSE), bis(triethoxysilyl)ethylene (hereinafter, BTSEY), bis-[3-(triethoxysilyl)tetrasulfide] (hereinafter, BTES), bis(triethoxysilyl)phenylene (hereinafter, BTEB), bis(triethoxysilyl)-biphenyl (hereinafter, BTEBP), 1,8-bis (triethoxysilyl)octane (hereinafter, BTEO), bis[3-(triethoxysilyl)propyl] tetrasulfide (hereinafter, BTEPT), N,N'-bis-[(3-triethoxysilylpropyl)aminocarbonylpolyethylene oxide] (hereinafter, BTEPEO), and the like. When the BTES, the BTEB, the BTEBP, the BTEO, the BTEPT, the BTEPEO, and the like are used as the organic silica precursor, properties of organic functional groups may be freely controlled by hybridizing various organic functional groups in a silica framework by changing only a type of the organic silica precursor without changing other synthetic protocols. Further, the porous organic silica layer may have an open core.

The step of selectively etching the inorganic silica may be included after the coating of the porous organic silica layer, thereby preparing the hollow mesoporous organic silica nanoparticle having the metal particles deposited thereon. The selective etching may be performed using hydrothermal etching.

In one implementation, the selective etching may be performed by heating aqueous solution in which the inorganic silica particles are dispersed.

In another implementation, the selective etching may be performed by heating basic aqueous solution in which the inorganic silica particles are dispersed. In the basic aqueous solution, a basic component may be selected from a group consisting of sodium hydroxide, potassium hydroxide, tetramethylammonium hydroxide, ammonia, sodium carbonate, sodium hydrogen carbonate, potassium carbonate, and potassium hydrogen carbonate.

As an example, the inorganic silica prepared using the TEOS is selectively etched using sodium carbonate aqueous solution as the basic aqueous solution based on a difference in a structure of the inorganic silica prepared using the TEOS, which is the inorganic silica precursor, and the porous organic silica layer formed by the CTAB and the BTSE. In addition, the CTAB, which is a meso channel guide material, is removed through ion exchange using ammonium nitrate in the ethanol solution. Thus, the hollow mesoporous organic silica nano/microparticle having the magnetic nanoparticles and/or the metal particles deposited thereon may be finally prepared.

Hollow Mesoporous Organic Silica Nano/Microparticle Having Different Types or Different Shapes of Metal Particles Simultaneously Deposited Thereon The hollow mesoporous organic silica nanoparticle having the metal particles deposited thereon of the present disclosure may be prepared by the method for preparing the hollow mesoporous organic silica nanoparticle having the metal particles deposited thereon of the present disclosure.

In the hollow mesoporous organic silica nano/microparticle having the metal particles deposited thereon, the metal may be the two or more types of metal, or the metal particles of the different shapes. The hollow mesoporous organic silica nano/microparticles having the metal particles deposited thereon may have the two or more different types of metal, or two or more different shapes of metal deposited thereon. For example, the metal particle may be in the form of the nanocube, the nanorod, the nanocage, and the like. As the metal, the gold (Au), the silver (Au), the palladium (Pd), the platinum (Pt), and the like may be used.

The hollow mesoporous organic silica nano/microparticle having the metal particles deposited thereon of the present disclosure may have not only a narrow size distribution and a high magnetic level, but also the meso channel present in the mesoporous organic silica layer and the hollow inner space. Further, the type of the metal particles may be freely tuned, and the metal particles may be deposited while adjusting a concentration of the metal particles.

The hollow mesoporous organic silica nano/microparticles having the metal particles deposited thereon of the present disclosure having the metal particles and the mesoporous organic silica shell has a wide range of applications such as catalysis, energy storage, and nano medicine.

In one implementation, in the hollow mesoporous organic silica nano/microparticle having the metal particles deposited thereon, the nano/microparticle may carry drug, and the nano/microparticle may be used as a drug carrier. In one implementation, when the metal is the gold in the hollow mesoporous organic silica nano/microparticle having the metal particles deposited thereon, the nano/microparticle may be used for photothermal therapy. In one implementation, when the metal is catalyst metal in the hollow mesoporous organic silica nano/microparticle having the metal particles deposited thereon, the nano/microparticle may be used as the catalyst.

Hereinafter, the hollow mesoporous organic silica nano/microparticles having the metal particles deposited thereon and the method for preparing the same of the present disclosure will be described in more detail with specific implementations.

Example 1

(1) Synthesis of $Fe_3O_4@SiO_2$—$NH_2$@AuNP

A core-shell $Fe_3O_4@SiO_2$ composite was prepared using the Stober method. First, ethanol dispersion (35 mL, 1.15 mg/mL) in which $Fe_3O_4$ is dispersed was put into a 50 mL self-standing falcon tube containing a mixture of 2.5 mL of deionized water and 3 mL of ammonia solution. Thereafter, 4 mL of ethanol solution in which 40 vol % of Tetraethyl orthosilicate (hereinafter, the TEOS) is present was rapidly injected into the mixture, and the mixture was reacted at room temperature for 1 hour while rotating at a speed of 10 rpm. Subsequently, the obtained $Fe_3O_4@SiO_2$ was filtered and collected, washed several times with the ethanol and the deionized water, and redispersed into 500 mL of deionized water. In order to functionalize a surface of the redispersed $Fe_3O_4@SiO_2$ with an amino group, (3-aminopropyl)trimethoxysilane (hereinafter, APTMS) (25 mL, 10 vol %) and 5 mL of ammonia solution were added into 500 mL of the $Fe_3O_4@SiO_2$ solution, and mechanically stirred at 40° C. for 12 hours to be reacted. Subsequently, $Fe_3O_4@SiO_2$—$NH_2$ to which the amino group functional group is attached was collected by filtration, washed several times with the ethanol and the deionized water, and re-dispersed again in 40 mL of deionized water. In order to decorate a surface of the $Fe_3O_4@SiO_2$—$NH_2$ with AuNP (Au Nano-Particles), after adding aqueous dispersion of AuNP (1 mL, 600 μg/mL) to 5 mL of the $Fe_3O_4@SiO_2$—$NH_2$ solution, the mixture was sonicated for 30 minutes and then vigorously stirred for 3 hours to obtain a product. Subsequently, the obtained product was collected by filtration, washed several times with the ethanol and the deionized water, and re-dispersed in 32.5 mL of 1-propanol for a next synthesis procedure, thereby obtaining $Fe_3O_4@SiO_2-NH_2@AuNP$, which is an inorganic silica particle to which a gold particle is attached.

(2) Synthesis of $Fe_3O_4@SiO_2-NH_2@AuNP@SiO_2$

Using a seeded silica growth method, the inorganic silica layer was coated on the $Fe_3O_4@SiO_2-NH_2@AuNP$ to prepare $Fe_3O_4@SiO_2-NH_2@AuNP@SiO_2$. Specifically, 32.5 mL of the obtained $Fe_3O_4@SiO_2-NH_2@AuNP$ solution was added into the 50 mL self-standing falcon tube containing the mixture of 2.5 mL of deionized water and 3 mL of ammonia solution. Thereafter, a 0.5 mL solution of 1-propanol in which 20 vol % of TEOS is present was rapidly injected into the mixture, and the mixture was reacted at room temperature for 1 hour while rotating at a speed of 10 rpm to obtain a product. Then, the obtained product was collected by filtration, washed several times with the methanol and the deionized water, and re-dispersed in 20 mL solution in which methanol and aqueous solution exist in 3:7 for a next synthesis procedure, thereby obtaining $Fe_3O_4@SiO_2-NH_2@AuNP@SiO_2$.

(3) Synthesis of $Fe_3O_4@SiO_2-NH_2@AuNP@SiO_2$.

The porous organic silica layer was coated on the $Fe_3O_4@SiO_2-NH_2@AuNP@SiO_2$. Specifically, mixed solution was prepared by mixing 20 mL of the $Fe_3O_4@SiO_2$-$NH_2@AuNP@SiO_2$ solution into a 50 mL self-standing falcon tube containing a mixture of 1.4 mL of methanol, 56 mg of CTAB, and 1 mL of ammonia solution. 0.3 mL of methanol solution in which 5 vol % of BTSE is present was rapidly injected into the mixed solution, and reacted at room temperature for 2 hours while rotating at a speed of 10 rpm. Then, the obtained product was collected by filtration, washed several times with the methanol and the deionized water, and re-dispersed in 20 mL of deionized water to obtain $Fe_3O_4@SiO_2-NH_2@AuNP@SiO_2@mSiO_2$, which is an inorganic silica particle having metal particles coated with the porous organic silica layer deposited thereon.

(4) Synthesis of $Fe_3O_4$/AuNP@YMOM

In order to selectively etch non-porous inorganic silica present inside the inorganic silica particle having the metal particles coated with the porous organic silica layer deposited thereon, 20 mL of the solution of $Fe_3O_4@SiO_2-$ $NH_2@AuNP@SiO_2@mSiO_2$ obtained above was heated up to 80° C. while being mechanically stirred, then $Na_2CO_3$ (3 mL, 40 mg/mL), which is basic aqueous solution, was added into 20 mL of the solution of $Fe_3O_4@SiO_2$- $NH_2@AuNP@SiO_2@mSiO_2$ to form a mixture, and then the mixture is selectively etched. After 1 hour of the etching, a product was obtained. The product was collected by magnet and washed several times with the deionized water. The CTAB, which is the surfactant, was extracted by rapid ion exchange, and treated in ethanol solution (20 mL, 6 mg/mL) in which the ammonium nitrate is present for 3 hours at 60° C. Further, in order to completely remove the CTAB, the above process was repeated twice to obtain a surfactant-free product. Finally, the surfactant-free product was collected by the magnet, washed several times with the deionized water, and dried at room temperature for later use, so that the hollow mesoporous organic silica nanoparticle having the metal particles deposited thereon according to example 1 of the present disclosure was finally obtained. The obtained hollow mesoporous organic silica nano/microparticles having the metal particles deposited thereon was referred to as $Fe_3O_4$/AuNP@YMOM.

[Property Analysis]

Analysis on structural properties, structural morphology, and properties of the $Fe_3O_4$/AuNP@YMOM, which is the hollow mesoporous organic silica nano/microparticles having the metal particles deposited thereon prepared according to Example 1, was performed.

(1) Scanning Electron Microscope Scanning Electron Microscope (SEM) Analysis

Morphology analysis of the $Fe_3O_4$/AuNP@YMOM prepared according to Example 1 was performed by a FE-SEM (SUPRA 25, EDAX, carl Zeiss Co, Germany). FIG. 1 shows a result of the morphology analysis.

FIG. 2 is a scanning electron microscope image of $Fe_3O_4$/AuNP@YMOM prepared according to Example 1 of the present disclosure.

Referring to FIG. 2, a scale bar in FIG. 2 is 5 µm. In addition, it may be seen that there is a narrow average diameter size distribution of 600 nm.

(2) Field-Emission Transmission Electron Microscopy (FE-TEM) Analysis

Using a FE-TEM (TALOS F200X, Thermofisher Scientific Co, USA) combined with energy dispersive spectrometry (an energy-dispersive X-RAY, EDX), structural and qualitative elemental analysis on the $Fe_3O_4$/AuNP@YMOM prepared according to Example 1 was performed. A result of the structural and qualitative element analysis is shown in FIG. 3.

FIG. 3 is field-emission transmission electron microscopy images of $Fe_3O_4$/AuNP@YMOM prepared according to Example 1 of the present disclosure.

First, Referring to a) in FIG. 3, it may be clearly seen that the $Fe_3O_4$/AuNP@YMOM prepared according to Example 1 of the present disclosure has a shape of a nanoparticle with a hollow structure in which the $Fe_3O_4$ and multiple AuNPs are uniformly located inside a mesoporous organic silica shell having a thickness of about 40 nm. An image inserted at a top of a) in FIG. 3 is a TEM image of the AuNP used in the preparation of $Fe_3O_4$/AuNP@YMOM in Example 1. When comparing the TEM image of the AuNP with a TEM image of the $Fe_3O_4$/AuNP@YMOM of the present disclosure, even when the $Fe_3O_4$/AuNP@YMOM was prepared by being subjected to a hot water treatment at 80° C. for 1 hour in $Na_2CO_3$ solution, because a morphological difference from the AuNP or a broken sphere is not observed, it may be seen that the $Fe_3O_4$/AuNP@YMOM was prepared without damage of the metal particles deposited thereon.

Referring to b) in FIG. 3, b) is a high-magnification TEM image of the $Fe_3O_4$/AuNP@YMOM prepared according to Example 1 of the present disclosure, and shows that the meso channel is oriented radially in the mesoporous organic silica shell toward a surface of the shell. That is, it may be seen that the $Fe_3O_4$/AuNP@YMOM has a mesoporous structure with a pore extending vertically from the core. Thus, it may be expected that injection of a guest molecule into an interior space may be preferred.

Referring to c) in FIG. 3, c) shows EDX elemental mapping images of the $Fe_3O_4$/AuNP@YMOM prepared according to Example 1 of the present disclosure. It may be seen that elements such as Si, Fe, Au, and the like corresponding to a composition of the synthesized material exist, and it may be seen that the hollow mesoporous organic silica nanoparticle having the $Fe_3O_4$ and the AuNP deposited thereon was prepared.

(3) X-ray Diffractometry (XRD)

In order to analyze a crystal phase of the $Fe_3O_4$/AuNP@YMOM prepared according to Example 1 of the present disclosure, x-ray diffractometry was performed using an x-ray diffractometer (an xpert3 diffractometer, Malvern Panalytical Ltd, UK) through Cu Kα radiation at 40 kV and 40 mA. A result thereof is shown in FIG. 4.

FIG. 4 is an image showing a XRD pattern of $Fe_3O_4$/AuNP@YMOM prepared according to Example 1 of the present disclosure.

Referring to FIG. 4, it may be seen that a diffraction peak of the $Fe_3O_4$/AuNP@YMOM is clearly distinguished from a diffraction peak of the $Fe_3O_4$, and it may be seen that characteristic peaks of the $Fe_3O_4$, the Au, and the silica appear in the diffraction peaks of the $Fe_3O_4$/AuNP@YMOM. It may be expected that the diffraction peaks of the $Fe_3O_4$/AuNP@YMOM appear resulted from the deposited $Fe_3O_4$ and AuNP. Therefore, it may be expected that the $Fe_3O_4$ and the AuNP are present in the $Fe_3O_4$/AuNP@YMOM.

(4) Nitrogen Sorption and Pore Size Analysis

In order to analyze nitrogen sorption and a pore size of the $Fe_3O_4$/AuNP@YMOM prepared according to Example 1 of the present disclosure, a description will be made with reference to FIG. 5.

FIG. 5 is a view showing a nitrogen sorption isotherm and a pore size distribution curve of the $Fe_3O_4$/AuNP@YMOM prepared according to Example 1 of the present disclosure.

In FIG. 5, it may be seen that the $Fe_3O_4$/AuNP@YMOM exhibits a type IV curve with a capillary condensation phase, which is a characteristic of a high surface area and a small pore size. A Brunauer-Emmett-Teller (hereinafter, a BET) surface area and a pore volume of the $Fe_3O_4$/AuNP@YMOM were calculated as 736.63 m2 $g^{-1}$ and 0.53 cm3 $g^{-1}$, respectively. It may seen from the pore size distribution graph that meso pores of the organic silica shell are uniform and have an average diameter size of about 2.4 nm.

(5) Magnetic Property Analysis

A magnetic property of the $Fe_3O_4$/AuNP@YMOM prepared according to Example 1 of the present disclosure will be described with reference to FIG. 6.

FIG. 6 is a view showing magnetic properties of $Fe_3O_4$/AuNP@YMOM prepared according to Example 1 of the present disclosure.

a) in FIG. 6 is a graph from which a magnetic property based on a magnetic field may be identified. It may be seen that a magnetic property graph of the iron magnetic particle $Fe_3O_4$ and a magnetic property graph of the $Fe_3O_4$/AuNP@YMOM having the $Fe_3O_4$ deposited thereon show similar patterns. Thus, it may be seen that the $Fe_3O_4$/AuNP@YMOM has a magnetic property because of the $Fe_3O_4$, which is the iron magnetic particles deposited on the nanoparticle. Further, b) in FIG. 6 is a view showing a result of separation using a magnet after dispersing the $Fe_3O_4$/AuNP@YMOM in a solvent. Referring to b) in 6, it may be seen that the $Fe_3O_4$/AuNP@YMOM uniformly dispersed in the solvent may be recovered quickly using the magnet. This is an experiment using the magnetic property of the $Fe_3O_4$/AuNP@YMOM. It may be seen from such experiment that the $Fe_3O_4$/AuNP@YMOM has the magnetic property.

(6) Photothermal Conversion

In order to quantitatively evaluate a concentration of the AuNP deposited on the $Fe_3O_4$/AuNP@YMOM prepared according to Example 1 of the present disclosure, a photothermal conversion efficiency of the $Fe_3O_4$/AuNP@YMOM aqueous suspension was measured under 635 nm laser irradiation. The $Fe_3O_4$/AuNP@YMOM aqueous suspension of a specific concentration was placed in a 200 µL microcentrifuge tube and irradiated with a 635 nm laser for 200 seconds at an output density of 0.55 W/cm². A temperature change and an IR image of the sample during the laser irradiation were recorded every 10 seconds using an infrared thermal imaging system (FLIR C3, FLIR Systems Inc, Korea), and a result thereof is shown in FIG. 7.

FIG. 7 shows thermal images of $Fe_3O_4$/AuNP@YMOM prepared according to Example 1 of the present disclosure.

Referring to FIG. 7, rapid heat generation within 70 seconds may be seen from the $Fe_3O_4$/AuNP@YMOM, so that it may be expected that the temperature increases rapidly under the irradiation with the laser. This proves that the $Fe_3O_4$/AuNP@YMOM may be applied as a photothermal carrier used in clinical applications of heat generation by the gold nanoparticle.

(7) Catalytic Reaction

In order to identify a catalytic reaction, FIG. 8 will be referred to.

FIG. 8 is a view showing catalytic reactions of $Fe_3O_4$/PdNP@YMOM and Comparative Samples prepared according to the present disclosure.

A hollow mesoporous organic silica nanoparticle having the palladium metal particles deposited thereon $Fe_3O_4$/PdNP@YMOM was prepared using a method substantially the same as the preparation method in Example 1 except for using 4 w % of Pd palladium particles as the metal particles.

Further, $Fe_3O_4$@$SiO_2$—$NH_2$@PdNP@$SiO_2$@m$SiO_2$, which is a comparative sample, was prepared using a method substantially the same as the preparation method of the $Fe_3O_4$/PdNP@YMOM except for the step of the selective etching.

Further, $Fe_3O_4$@$SiO_2$—$NH_2$@PdNP, which is a comparative sample, was prepared using a process substantially the same as the preparation method of the $Fe_3O_4$@$SiO_2$—$NH_2$@PdNP@$SiO_2$@m$SiO_2$ except for a step of coating a silica layer on a metal-attached silicon particle and coating a porous organic silica layer on the silica layer.

a) in FIG. 8 shows TEM images of the $Fe_3O_4$@$SiO_2$—$NH_2$@PdNP, the $Fe_3O_4$@$SiO_2$—$NH_2$@PdNP@$SiO_2$@m$SiO_2$, and the $Fe_3O_4$/PdNP@YMOM from the left.

For the prepared $Fe_3O_4$/PdNP@YMOM, the $Fe_3O_4$@$SiO_2$—$NH_2$@PdNP, and the $Fe_3O_4$@$SiO_2$—$NH_2$@PdNP@$SiO_2$@m$SiO_2$, the catalytic reactions were performed as follows. An aqueous dispersion of the $Fe_3O_4$/PdNP@YMOMs (10 mL, 10 m/mL) was added to a 50 mL self-standing falcon tube containing $NaBH_4$ aqueous solution (10 mL, 0.05 M). Then, 4-nitrophenol (hereinafter, 4-NP) aqueous solution (140 µL, 0.01 M) was added thereto and reacted immediately. A UV-vis spectroscopy was used to monitor a change in absorption during the reaction. For comparative studies, the same process was repeated for the $Fe_3O_4$@$SiO_2$—$NH_2$@PdNP and the $Fe_3O_4$@$SiO_2$—$NH_2$@PdNP@$SiO_2$@m$SiO_2$, and a result thereof is shown in b) and c) in FIG. 8.

Referring to b) in FIG. 8, it may be seen that a reduction efficiency of the $Fe_3O_4$/PdNP@YMOMs is much higher than that of the $Fe_3O_4$@$SiO_2$—$NH_2$@PdNP and the $Fe_3O_4$@$SiO_2$—$NH_2$@PdNP@$SiO_2$@m$SiO_2$. More specifically, it may be seen in b) that a k value 0.332 $min^{-1}$ of the $Fe_3O_4$/PdNP@YMOMs is about 2.6 times a k value 0.129 $min^{-1}$ of the $Fe_3O_4$@$SiO_2$—$NH_2$@PdNP, and the $Fe_3O_4$@$SiO_2$—$NH_2$@PdNP@$SiO_2$@m$SiO_2$ has a value of almost zero because the catalytic reaction does not occur as internal non-porous silica prevents a reactant from reaching a Pd surface.

It may be expected that an excellent catalytic performance of the $Fe_3O_4$/PdNP@YMOMs compared to the $Fe_3O_4$@$SiO_2$—$NH_2$@PdNP is mainly due to the Pd palladium particles well dispersed independently in the hollow space. Thus, it may be seen that the $Fe_3O_4$/PdNP@YMOMs has a high catalytic reaction rate because the $Fe_3O_4$/PdNP@YMOMs has a much higher catalytic activity surface area. Such result reflects that the uniform vertical meso channels of the organic silica layer facilitate high-rate diffusion and transport of the reactant and the product molecule.

[Comparative Analysis]

For comparative analysis, Sample-1 of a hollow mesoporous organic silica nanoparticle having the Au and the $Fe_3O_4$ deposited thereon prepared by the method for preparing the hollow mesoporous organic silica nanoparticle having the metal particles deposited thereon of the present disclosure was prepared.

FIG. 9 is a view showing methods for preparing Sample-1 and Comparative Sample-1 prepared according to the present disclosure. The preparation method of Sample-1 will be described with reference to a) in FIG. 9.

a) in FIG. 9 is a schematic diagram showing the preparation method of Sample-1 prepared using the method for preparing the hollow mesoporous organic silica nanoparticle having the metal particles deposited thereon of the present disclosure.

Referring to a) in FIG. 9, Sample-1 was prepared using the method for preparing the hollow mesoporous organic silica nanoparticle having the metal particles deposited thereon of the present disclosure. Sample-1 was obtained using a method of firstly attaching the metal particles using a metal attachment functional group present on a surface of the silica particle containing the $Fe_3O_4$, then coating the inorganic silica layer to completely cover the metal particles, then coating the inorganic silica layer with a porous organic silica layer, and then selectively etching the inorganic silica layer.

Further, in order to compare with this, Comparative Sample-1 of the hollow mesoporous organic silica nanoparticle having the Au and the $Fe_3O_4$ deposited thereon was prepared. A method for preparing Comparative Sample-1 will be described with reference to b) in FIG. 9.

b) in FIG. 9 is a schematic diagram showing the preparation method of Comparative Sample-1.

Referring to b) in FIG. 9, Comparative Sample-1 of the hollow mesoporous organic silica nanoparticle having the Au and the $Fe_3O_4$ deposited thereon was prepared using a method of attaching the metal particles using the metal attachment functional group present on the surface of the silica particle containing the $Fe_3O_4$, directly coating the porous organic silica layer without coating the inorganic silica layer to cover the metal, and performing the selectively etching.

For comparative analysis of Sample-1 and Comparative Sample-1 nanoparticles prepared using different methods, each of which was analyzed using a transmission electron microscopy (TEM). a result thereof is shown in FIG. 10.

FIG. 10 shows TEM images of Sample-1 and Comparative Sample-1 prepared according to the present disclosure.

When comparing Sample-1 and Comparative Sample-1 with each other with reference to FIG. 10, it may be seen in a) in FIG. 10 showing Sample-1 of the nanoparticle prepared using the preparation method of the present disclosure that the gold nanoparticles are freely dispersed in the inner cavity without sinking into the mesoporous organic silica shell. On the other hand, it may be seen in b) in FIG. 10 showing Comparative Sample-1 that the gold nanoparticles are sinking or are being fixed at the interior or the interface of the mesoporous organic silica shell, and thus, the gold nanoparticles are not freely dispersed in the defined inner cavity.

The difference between the nanoparticles prepared using the preparation methods of Sample-1 and Comparative Sample-1 as described above is very important in two aspects. First, when the inorganic nanoparticle used as the catalysts is deposited on the nanoparticle, in the case of the preparation without the coating of the inorganic silica layer for covering the metal as in the preparation method of Comparative Sample-1, because the inorganic nanoparticle sinks and is buried into and present in the mesoporous organic silica layer, a contact area with the reactant is lowered, so that a catalytic activity may be deteriorated or a function as the catalyst may be lost. Second, in the case of the preparation as in the preparation method of Comparative Sample-1, there is a problem that a space in which the inorganic nanoparticle is deposited is limited to an inner surface of the inner cavity. The nanoparticle prepared using the preparation method of the present disclosure has an advantage of dramatically increasing an absolute amount of catalyst that may be deposited because an entirety of the inner cavity becomes a space in which the catalyst may be dispersed.

[Application]

(1) Hollow Mesoporous Organic Silica Nanoparticle Having Various Shapes and Various Types of Metal Particles Deposited Thereon In order to identify that the metal is the two or more types of metal or the metal particles of different shapes, and that the at least two different types of metal or the at least two different shapes of metal may be deposited on the hollow mesoporous organic silica nanoparticle having the metal particles deposited thereon prepared according to the present disclosure, a description will be made with reference to FIG. 10.

FIG. 11 shows TEM images of hollow mesoporous organic silica nano/microparticles having various types of metal particles deposited thereon prepared according to the present disclosure.

Referring to FIG. 11, it may be seen that a) in FIG. 11 is a hollow mesoporous organic silica nanoparticle having spherical gold particles and magnetic nanoparticles deposited thereon, b) is a hollow mesoporous organic silica nanoparticle having nanoroad-shaped gold particles and magnetic nanoparticles deposited thereon, and c) is a hollow mesoporous organic silica nanoparticle having nanocube-shaped gold particles and magnetic nanoparticles deposited thereon. Thus, it may be seen that the hollow mesoporous organic silica nanoparticle having the metal particles deposited thereon prepared using the preparation method of the present disclosure may have the metal particles and the magnetic nanoparticles having various shapes deposited thereon.

d) in FIG. 11 is an image of a hollow mesoporous organic silica nanoparticle having nanocube-shaped palladium and magnetic nanoparticles. It may be seen from d) that not only the gold particles but also various kinds of metal particles may be deposited.

e) in FIG. 11 shows a composite hollow mesoporous organic silica nanoparticle having not only magnetic nanoparticles and spherical gold nanoparticles, but also a palladium nanocubes simultaneously deposited thereon.

It may be expected from FIG. 11 that the nanoparticle prepared using the method for preparing the hollow mesoporous organic silica nanoparticle having the metal particles deposited thereon of the present disclosure is very remarkable in terms of the shape of the deposited metal nanoparticles compared to that prepared using the conventional nanoparticle synthesis method. Thus, it may be seen that various shapes of metal nanoparticles that have already been synthesized may be deposited.

Further, it was identified that two or more types of metal nanoparticles with different shapes and components may be deposited on the mesoporous layer. Thus, it may be expected that the present disclosure has a very high applicability to a medical field by introducing additional metal nanoparticles capable of performing various functions such as a biocatalytic reaction, an MRI, and the like by depositing not only the gold nanoparticle, but also a metal nanoparticles having a completely different function. Further, the mesoporous organic silica nanoparticle having such metal particles deposited thereon has great significance in enabling complex functions to be implemented in the single nanoparticle structure.

(2) Hollow Mesoporous Organic Silica Nanoparticle Having Metal Particles of an Adjusted Concentration In order to identify that the metal particles may be deposited while varying the concentration thereof based on the preparation according to the method for preparing the hollow mesoporous organic silica nanoparticle having the metal particles deposited thereon of the present disclosure, a description will be made with reference to FIG. 11.

FIG. 12 shows TEM images of a hollow mesoporous organic silica nano/microparticle having metal particles with an increased content deposited thereon.

Referring to FIG. 12, it may be identified that the nanoparticle was prepared by increasing the content of the injected metal particles from 0 to 21.95 μmol through the preparation method according to the present disclosure, and an increased amount of metal particles is deposited as an amount of the injected metal increases. Thus, it may be expected that the concentration of the metal particles may be precisely controlled.

(3) Application of Drug Releasing Material

In addition to the fact that the hollow mesoporous organic silica nanoparticle having the metal particles deposited thereon of the present disclosure may have various inorganic nanoparticles deposited inside the hollow, because an oil material may be post-encapsulated through the mesoporous organic silica layer, the hollow mesoporous organic silica nanoparticle having the metal particles deposited thereon of the present disclosure may be applied as a photo-stimulative drug releasing material of micron to submicron size by combining a photothermal effect of the metal particles and a phase change function based on a temperature of a phase change material (hereinafter, PCM) with each other.

FIG. 13 is a view related to a photo-stimulative drug releasing material using a hollow mesoporous organic silica nano/microparticle prepared according to the present disclosure. a) in FIG. 13 is a schematic diagram of a preparation process of a photo-stimulative drug releasing material using a hollow mesoporous organic silica nanoparticle prepared according to the present disclosure. b) in FIG. 13 is a diagram showing utilization of a photo-stimulative drug releasing material using a hollow mesoporous organic silica nanoparticle prepared according to the present disclosure.

Referring to b in FIG. 13, it may be identified that the hollow mesoporous organic silica nanoparticle having the gold particles and the magnetic particles deposited thereon prepared according to the present disclosure may be utilized as the photo-stimulative drug releasing material by encapsulating an anti-cancer substance dissolved in the liquid PCM into the mesoporous organic silica layer through the mesoporous organic silica shell at an elevated temperature of about 60° C., and then cooling the anti-cancer substance at room temperature to change a phase of the PCM to solid. Specifically, because the PCM has the solid phase at about 36° C., which is a human body temperature, even when being injected into cancer cells, the encapsulated anti-cancer substance is not released to the outside through the meso pores. When drug release is necessary, the hollow mesoporous organic silica nanoparticle having the gold particles and the magnetic particles deposited thereon irradiates NIR to increase a temperature of the by about 45° C. or more to change the phase of the PCM to liquid, and thus, allows the internal drug to be released to the outside, so that the hollow mesoporous organic silica nanoparticle having the gold particles and the magnetic particles deposited thereon is utilized as the drug releasing material. When the NIR irradiation is stopped, the phase of the PCM is changed back to the solid as the temperature drops to the body temperature, and thus, the drug release stops. In this way, it may be expected that the hollow mesoporous organic silica nanoparticle having the gold particles and the magnetic particles deposited thereon may be used as the photo-stimulative drug releasing material that may selectively adjust the drug release by irradiating the NIR as needed. In this connection, the magnetic particles that may be selectively deposited may be used in a variety of purposes, such as tracking or visualization of substances through the MRI, recovery using the magnet, or the like.

(4) Utilization of Tandem Micro Reactor

A fact that the hollow mesoporous organic silica nanoparticle having the metal particles deposited thereon prepared according to the present disclosure may be utilized as a micro reactor in which heterogeneous inorganic catalysts are encapsulated will be described with a specific approach through FIG. 14.

FIG. 14 is a view showing utilization as a tandem micro reactor of a hollow mesoporous organic silica nano/microparticle having metal particles deposited thereon according to the present disclosure.

Referring to FIG. 14, it may be identified that the hollow mesoporous organic silica nano/microparticle having the metal particles deposited thereon prepared according to the present disclosure may be used as a tandem catalyst by depositing the heterogeneous inorganic catalysts into one hollow micro-reactor. Therefore, it may be identified that it is possible to construct a microreactor capable of catalyzing two or more chemical reactions in a complementary relationship at a micron level.

The present disclosure has been described with reference to the preferred embodiments of the present disclosure. Those skilled in the art will understand that the present disclosure may be variously modified and changed without departing from the spirit and scope of the present disclosure as described in the following claims.

What is claimed is:

1. A method for preparing a hollow mesoporous organic silica nano/microparticle having metal particles deposited thereon, the method comprising:
   coating a porous organic silica layer on a surface of an inorganic silica particle having the metal particles deposited thereon to form a coated particle; and
   selectively etching the inorganic silica to remove the inorganic silica from the coated particle, thereby forming the hollow mesoporous organic silica nano/microparticle having metal particles deposited thereon;

wherein the inorganic silica particle having the metal particles deposited thereon is prepared by a method including:
modifying the surface of the inorganic silica particle with a metal-affinity functional group to prepare an inorganic silica particle having the metal-affinity functional group introduced on the surface of the inorganic silica;
attaching the metal particles to the metal affinity functional group to prepare an inorganic silica particle with the metal particles attached thereto; and
coating an inorganic silica layer on the inorganic silica particle with the metal particles attached thereto.

2. The method of claim 1, wherein the inorganic silica particle contains magnetic nanoparticles therein.

3. The method of claim 1, wherein the metal-affinity functional group is one of an amine group and a thiol group.

4. The method of claim 1, wherein the inorganic silica is synthesized from tetraethyl orthosilicate (TEOS).

5. A method for preparing a hollow mesoporous organic silica nano/microparticle having metal particles deposited thereon, the method comprising:
coating a porous organic silica layer on a surface of an inorganic silica particle having the metal particles deposited thereon; and
selectively etching the inorganic silica to remove the inorganic silica;
wherein the inorganic silica particle having the metal particles deposited thereon is prepared by a method including:
modifying the surface of the inorganic silica particle with a metal-affinity functional group to prepare an inorganic silica particle having the metal-affinity functional group introduced on the surface of the inorganic silica;
attaching the metal particles to the metal affinity functional group to prepare an inorganic silica particle with the metal particles attached thereto; and
coating an inorganic silica layer on the inorganic silica particle with the metal particles attached thereto; and
wherein the metal-affinity functional group is introduced from a member selected from the group consisting of (3-aminopropyl)trimethoxysilane (APTMS), (3-aminopropyl)triethoxysilane (APTES), (3-mercaptopropyl)trimethoxysilane (MPTMS) and (3-mercaptopropyl)triethoxysilane (MPTES).

6. The method of claim 1, wherein the coating of the inorganic silica layer on the inorganic silica particle with the metal particles attached thereto includes the step of coating the inorganic silica layer to cover all of the metal particles.

7. The method of claim 1, wherein the porous organic silica layer has an open core.

8. The method of claim 1, wherein the coating of the porous organic silica layer is synthesized from solution of an organic silica precursor and a surfactant mixed with each other.

9. The method of claim 8, wherein the organic silica precursor comprises at least one member selected from the group consisting of bis(triethoxysilyl)ethane (BTSE), bis(triethoxysilyl)ethylene (BTSEY), bis-[3-(triethoxysilyl)tetrasulfide] (BTES), bis(triethoxysilyl)phenylene (BTEB), bis(triethoxysilyl)-biphenyl (BTEBP), 1,8-bis(triethoxysilyl)octane (BTEO), bis[3-(triethoxysilyl)propyl] tetrasulfide (BTEPT) and N,N'-bis-[(3-triethoxysilylpropyl)aminocarbonylpolyethylene oxide] (BTEPEO).

10. The method of claim 8, wherein the surfactant comprises at least one member selected from the group consisting of hexadecyltrimethylammonium bromide (CTAB), cetyltrimethylammonium chloride (CTAC), sodium dodecyl sulfate (SDS), polysorbates and triton.

11. The method of claim 1, wherein the selective etching is performed by heating aqueous solution containing the dispersed inorganic silica particles.

12. The method of claim 1, wherein the selective etching is performed by heating basic aqueous solution containing the dispersed inorganic silica particles.

13. The method of claim 12, wherein a basic component in the basic aqueous solution is selected from the group consisting of sodium hydroxide, potassium hydroxide, tetramethylammonium hydroxide, ammonia, sodium carbonate, sodium hydrogen carbonate, potassium carbonate and potassium hydrogen carbonate.

14. A hollow mesoporous organic silica nano/microparticle having metal particles deposited thereon prepared according to the method of claim 1.

15. The hollow mesoporous organic silica nano/microparticle of claim 14, wherein the metal particle includes at least two types of metal particles or includes different shapes of metal particles, and
wherein the at least two types of metal particles or the different shapes of metal particles are deposited thereon the hollow mesoporous organic silica nano/microparticle.

16. The hollow mesoporous organic silica nano/microparticle of claim 15, wherein the metal is gold.

17. The hollow mesoporous organic silica nano/microparticle of claim 15, wherein the metal is catalyst metal.

18. The hollow mesoporous organic silica nano/microparticle of claim 15, wherein the nano/microparticle carries a drug.

19. A method for preparing a hollow mesoporous organic silica nano/microparticle having metal particles deposited thereon, the method comprising:
coating a porous organic silica layer on a surface of a non-porous inorganic silica particle having the metal particles deposited thereon; and
selectively etching non-porous inorganic silica present in an inside the inorganic silica particle having the metal particles coated with the porous organic silica layer deposited thereon to form the hollow mesoporous organic silica nano/microparticle having metal particles deposited thereon;
wherein the non-porous inorganic silica particle having the metal particles deposited thereon is prepared by a method including:
modifying the surface of the inorganic silica particle with a metal-affinity functional group to prepare an inorganic silica particle having the metal-affinity functional group introduced on the surface of the inorganic silica;
attaching the metal particles to the metal affinity functional group to prepare an inorganic silica particle with the metal particles attached thereto; and
coating an inorganic silica layer on the inorganic silica particle with the metal particles attached thereto.

20. The method of claim 1, further comprising adding a drug to the hollow mesoporous organic silica nano/microparticle having metal particles deposited thereon.

* * * * *